US009345825B2

(12) United States Patent
Herrenbauer et al.

(10) Patent No.: US 9,345,825 B2
(45) Date of Patent: May 24, 2016

(54) DIALYSIS DEVICE

(75) Inventors: Michael Herrenbauer, Neu-Anspach (DE); Robert Pohlmeier, Bad Homburg (DE)

(73) Assignee: FRESENIUS MEDICAL CARE DEUTSCHLAND GMBH, Bad Homburg (DE)

(*) Notice: Subject to any disclaimer, the term of this patent is extended or adjusted under 35 U.S.C. 154(b) by 751 days.

(21) Appl. No.: 13/377,316

(22) PCT Filed: Jun. 9, 2010

(86) PCT No.: PCT/EP2010/058071
§ 371 (c)(1), (2), (4) Date: Dec. 9, 2011

(87) PCT Pub. No.: WO2010/142717
PCT Pub. Date: Dec. 16, 2010

(65) Prior Publication Data
US 2012/0097587 A1 Apr. 26, 2012

(30) Foreign Application Priority Data
Jun. 10, 2009 (DE) ......................... 10 2009 026 901

(51) Int. Cl.
*B01D 61/24* (2006.01)
*A61M 1/16* (2006.01)
(Continued)

(52) U.S. Cl.
CPC ............... *A61M 1/16* (2013.01); *A61M 1/1633* (2014.02); *A61M 1/3437* (2014.02)

(58) Field of Classification Search
CPC ....... A61M 1/14; A61M 1/16; A61M 1/1621; A61M 1/1623; A61M 1/1633; A61M 1/1696; A61M 1/1694; B01D 25/00; B01D 25/001; B01D 29/00; B01D 29/0002; B01D 29/0004; B01D 29/01; B01D 29/05; B01D 29/50; B01D 29/56; B01D 61/00; B01D 61/02; B01D 61/022; B01D 61/025; B01D 61/027; B01D 61/08; B01D 61/14; B01D 61/142; B01D 61/145; B01D 61/24; B01D 61/243; B01D 61/246; B01D 61/28; B01D 61/30; B01D 61/32; B01D 61/58; B01D 63/00; B01D 63/08; B01D 63/082; B01D 2317/02; B01D 2317/025; B01D 2317/06; B01D 2317/08
USPC ......... 210/767, 790, 805, 806, 321.6, 321.71, 210/321.72, 321.75, 321.84, 500.21, 500.1
See application file for complete search history.

(56) References Cited

U.S. PATENT DOCUMENTS 3,619,423 A 11/1971 Galletti et al.
3,799,873 A 3/1974 Brown
(Continued)

FOREIGN PATENT DOCUMENTS

DE 4224963 2/1994
DE 195 40 079 4/1997
(Continued)

OTHER PUBLICATIONS

Palevsky et al, "The Acute Dialysis Quality Initiative—Part V: Operational Characteristics fo CRRT" Advances in Renal Replacement Therapy, vol. 9, No. 4, Oct. 2002, pp. 268-272.
(Continued)

*Primary Examiner* — Allison Fitzsimmons
(74) *Attorney, Agent, or Firm* — Jacobson Holman, PLLC.

(57) ABSTRACT

The invention relates to a dialysis device (1) having a dialysate circuit comprising a first dialyzer (3) and a second dialyzer (5) wherein the first dialyzer (3) is connectable to a blood circulation of a patient via a blood feed line (11) and a recirculation (13), an effluent for a retentate flow ($Q_{effluent}$) from the dialysate circuit to the second dialyzer (5) is provided and a permetate stream ($Q_{out}$) of the second dialyzer (5) in the dialysate circuit is passed to the first dialyzer (3), the second dialyzer (5) comprising a filter membrane having a cut-off value of at least 500 Da and the first dialyzer (3) comprising a filter membrane having a cut-off value exceeding that of the second dialyzer (5).

12 Claims, 2 Drawing Sheets

Figure 1:
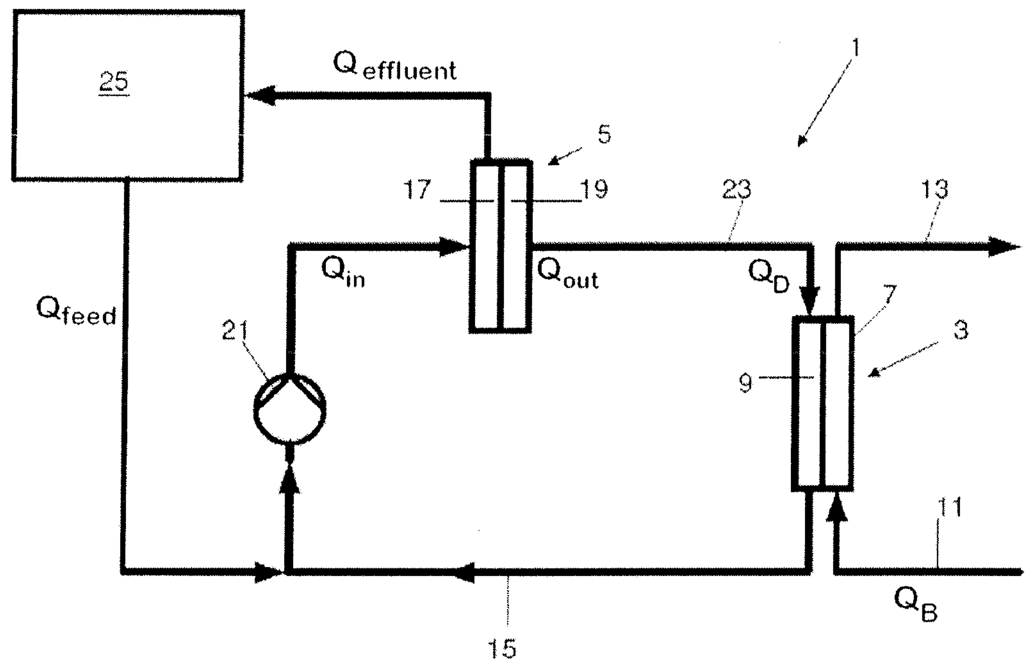

(51) Int. Cl.
*A61M 1/34* (2006.01)
*A61M 1/14* (2006.01)

(56) References Cited

U.S. PATENT DOCUMENTS

| | | | |
|---|---|---|---|
| 3,799,973 A | 3/1974 | Smith | |
| 5,660,722 A | 8/1997 | Nederlof | |
| 6,406,631 B1 * | 6/2002 | Collins et al. | 210/646 |
| 6,561,997 B1 * | 5/2003 | Weitzel et al. | 604/6.09 |
| 7,976,709 B2 * | 7/2011 | Wallenas | A61M 1/1696 210/259 |
| 2004/0182787 A1 * | 9/2004 | Chevallet et al. | 210/646 |
| 2006/0041216 A1 | 2/2006 | McLaughlin et al. | |

FOREIGN PATENT DOCUMENTS

| | | |
|---|---|---|
| JP | H08332222 | 12/1996 |
| JP | H1071201 | 3/1998 |
| JP | 2006-520635 | 9/2006 |
| JP | 2008-510511 | 4/2008 |
| JP | 2008-529715 | 8/2008 |
| JP | 2010-512939 | 4/2010 |
| WO | WO 2004/082733 | 9/2004 |
| WO | WO 2006/088419 | 8/2006 |

OTHER PUBLICATIONS

Ricci et al, "Solute removal during continuous renal replacement therapy in critically ill patients: convection versus diffusion" Critical Care 2006, vol. 10, No. 2, pp. 1-7.

* cited by examiner

DIALYSIS DEVICE

This is a national stage of PCT/EP10/058071 filed June 9, 2010 and published in German, which claims the priority of German number 10 2009 026 901.0 filed June 10, 2009, hereby incorporated by reference.

The present invention relates to a dialysis device having a dialysate circuit comprising a first dialyzer, the first dialyzer being connectable to the blood circulation of a patient via a blood feed line and a recirculation line, wherein in the second dialyzer an effluent to a retentate flow ($Q_{effluent}$) from the dialysate circuit is provided and a permeate stream ($Q_{out}$) of the second dialyzer in the dialysate circuit is passed to the first dialyzer as well as a device for dialysis comprising a dialysate circuit including connecting means for a first dialyzer and for a second dialyzer, wherein the first dialyzer is connectable to a blood feed line and a recirculation line, and an effluent for a retentate stream ($Q_{effluent}$) from the dialysate circuit is provided at the connected second dialyzer.

Dialysis devices which are disclosed in this specification are known in the art and are used for blood-cleansing in case of renal failure. Removal of medium-sized molecules, such as for example myoglobin or interleukins which are also called middle molecules is of special importance during acute renal failure. Such middle molecules have molecular weights of e.g. 1,000 to 50,000 Da (Dalton). Whereas, in the case of renal failure, removal of smaller molecules, i.e. molecules having molecular weights lower than 1000 Da on a predetermined level will be sufficient. Thus, what is essential with acute renal failure is efficient removal of middle molecules as well.

Among dialysis processes distinction is essentially made between hemofiltration and hemodialysis. With hemodialysis exchange of matter and consequently cleansing of the blood will take place by diffusion whereas with hemofiltration cleansing will be accomplished by convective transport of matter. Convective transport of matter has been shown to have higher clearance of middle molecules than diffusive transport of matter, the clearance identifying the volume which will be removed from the respective substance. Generally a process of hemofiltration is preferred to hemodialysis during acute renal failure. However the process of hemofiltration shows some serious disadvantages compared to hemodialysis.

Consequently with hemodialysis the blood plasma removed by filtration will be replaced by a substitute solution spending 1-8 l of substitute solution per hour. However clinicians are generally required to transfer this solution in the form of bags of 4.5-5 l capacity to the location where treatment will take place. Additionally, following this treatment the bags have to be discarded thereby causing high expenditure of work and costs.

Moreover sufficiently high blood flows are required for hemofiltration. Patients suffering from chronic renal failure generally have a so called artherio-venous shunt, i. e. an artificial access enabling blood flows between 300-400 ml/min. Patients suffering from acute renal failure rarely dispose of such an access and consequently only blood flows of 100-200 ml/min will be reached. The blood flow required for effective hemofiltration typically causes numerous alarms due to vesicular access problems with patients. These alarms subsequently must be eliminated by the clinical staff, thereby causing additional expenditure of work.

Convective transport is a further disadvantage of hemofiltration, causing faster clogging of the dialysis filter; which is also called filter-clogging, compared to the diffuse exchange in hemodialysis. Accordingly, during long-term treatment filters have to be exchanged more frequently which in turn will add to costs and expenditure of work for the treatment.

Finally a further disadvantage of hemofiltration resides in that, depending on the hemofilter used, the patient during treatment may suffer from a significantly higher loss of albumin than with hemodialysis. In addition the substitute solutions required for hemofiltration are regulated by the Pharmaceutical Drug Law limiting versatility in practical personalizing of care.

Briefly, it turned out that work burden for clinicians and costs of treatment is very high with hemofiltration, such that this procedure will strongly be limited in practical use.

Devices and processes have been proposed in the art for nevertheless accomplishing high clearance of middle molecules while spending only low amount of solution, thus achieving low cost and reduced expenditure of work. From WO 2004/082733 for example a process of hemofiltration is known wherein two filters are arranged in a cascade-like shape. Herein the filtrate obtained from the first filter will be refiltrated in the second filter. The filtrate obtained from the second filter will subsequently be recirculated in predilution to the blood of the patient as a substitute solution. By retaining middle molecules of the first filtrate on the second filter a substitute solution having reduced number of middle molecules will be supplied to the blood. It is true that the amount of substitute solution required will thus be reduced and the number of middle-sized molecule will be lowered, however, what is disadvantageous is the fact that effectiveness of operation concerning middle molecules is not ideal due to dilution of the blood before filtration.

It is thus an object of the present invention to realize a dialysis device which is operational effective and inexpensive and provides for efficient removal of middle-sized molecules even at low blood flow, with little effort.

In order to achieve this object a dialysis device having the features according to claim 1 is proposed. The dialysis device has a dialysate circuit comprising a first dialyzer and a second dialyzer, the first dialyzer being connectable to the blood circulation of the patient by way of blood feeding and recirculation means. The second dialyzer comprises a filter membrane having a cut-off value of at least 500 Da and the first dialyzer comprises a filter membrane having a higher cut-off value than the second dialyzer.

The retentate represents the portion of the dialysate which will be fed to the second dialyzer and will not permeate the membrane in the second dialyzer but will be removed from the dialysate and will be discarded. By filter membrane the membrane of any fluid filter is meant which, depending on the particle (or molecule) size, is suitable to filter off a portion of the flow. The second dialyzer may also be referred to as a dialyzing filter since, at the second dialyzer, the amount of filtrate introduced to the second dialyzer will be separated into two streams, as will be explained in detail below.

A cut-off value is a parameter of the filter membrane which is related to the pore size thereof. Molecules the masses of which exceed a respective cut-off value of the filter will not be able to permeate the membrane at all or will permeate the membrane to a negligibly low extend. Thus said cut-off value of 500 Da may be understood as a maximum pore size of the filter of 0.001-0.005 μm. For example electrolytes (such as Ca, Na, phosphate or equivalent ions) have masses in the order of 100 Da. Since the cut-off value of the second filter is significantly higher than this size of electrolytes the latter will not be retained in the second dialyzer, thus especially providing for the removal of middle-sized molecules from the blood stream, as will be detailed below. Alternatively to the definition of the cut-off value of 500 Da according to the claim it will also be understood according to the invention that electrolyte concentration in the permeate stream of the second dialyzer will essentially remain unchanged based on the feed of filtration thereto, the latter being the amount to be introduced to the second dialyzer.

As a result, as will be detailed below, middle size molecules of 1-50 kDa and most preferably 5-25 kDa will increasingly be withdrawn from the blood stream.

All in all, the aforementioned advantages of hemofiltration will broadly be realized by the disclosed dialysis device and at the same time the above-mentioned drawbacks of hemodialysis are avoided.

Additionally, with the device disclosed herein, due to introducing the filtrate from the second dialyzer into the blood of the patient in predilution, the advantage of avoiding decrease of operational effectiveness in regard to the middle molecules will arise. Instead, the used filtrate will partially be regenerated and reused as a dialysate, thereby being able to save on fresh dialysate what consequently will allow lower-cost treatment. Furthermore, with the device according to the invention, the advantage arises that the employed dialysate has to be conform to the regulatory requirements of the Medical Devices Act and to the benefits of versatility associated therewith, since it will not be directly added to the blood but rather will remain circulating in the dialysate circuit. Thus, according to two embodiments of the present invention utilization of a substitute solution falling under the Pharmaceutical Drug Law will not be required. Due to different approval methods for dialysate the latter may be adapted to medical requirements more rapidly, such as for example addition of phosphate or the like. Furthermore substitute fluids are only available in the form of 5 liter bags. Instead, according to the present invention, use of dialysate which will be formulated online from concentrate and water and which may be supplied from a central supply unit or which may be provided as a batch of 30-100 l in place is possible. Furthermore the device is also suitable for weak blood streams thereby causing fewer alarms associated with vesicular access problems. This also adds to improved treatment and reduced expenditure of work. Since only minor convective mass transport will occur, for example as part of the required dehydration, with this device, the filter will remain operable for a longer period of time, thereby reducing both waste of material and expenditure of work. The process based on diffusion which is realized by the present device will reduce loss of albumin for the patient. Thus the present process will attain significant improvement for the patient as well as operational effectiveness.

In a preferred embodiment of the present invention fresh dialysate (herein in the following also called dialysate substitute) will be introduced into the dialysate recovered by filtration in order to compensate flow of retentate. The addition of dialysate substitute may occur both upstream and downstream of the second dialyzer, as seen in the flow direction of the dialysate. Addition of dialysate substitute upstream of the second dialyzer in the extracorporeal dialysate cycle will especially be preferred because the second dialyzer thereby, on the one hand, functions as a regenerator for the dialysate from the first dialyzer and, on the other hand, functions as a dialysate filter for removal of bacteria and endotoxins from the dialysate substitute. Consequently the second dialyzer has dual function, and in addition will be operable as a sterile filter for the fresh dialysate, thereby increasing quality of the dialysate; and an additional dialysate filter may be omitted.

In one alternative embodiment of the dialysis device a feed of dialysate substitute into the dialysate cycle downstream of the second dialyzer and upstream of the first dialyzer (3) is provided. Thereby effective use will be made of the dialysate substitute since it will immediately be introduced into the first dialyzer without reducing its quantity by filtration in the second dialyzer.

Thus, the two embodiments wherein both partially regenerated dialysate and fresh dialysate are co-introduced into the dialysate space of the first dialyzer are especially beneficial. Hereby, supplying of fresh dialysate upstream of the second dialyzer, as seen in the flow direction of the dialysate, provides significant benefits, because in this way an additional filter for cleansing of fresh dialysate may be omitted. The function of cleansing will additionally be taken over by the second dialyzer.

In another alternative embodiment introduction of a substitute solution into the blood circulation is provided; wherein introduction advantageously will occur upstream of the first dialyzer, as seen in flow direction. This means that an amount of substitution fluid will be introduced into the blood and will be transferred to the dialysate circuit in the first dialyzer, which amount largely corresponds to the retentate effluent in the second dialyzer. Due to the larger amount thus being conveyed within the first dialyzer blood cleansing may also be improved. Furthermore the desired composition of blood may thereby be controlled in a more straightforward way and may optionally be optimized by additional application of drugs.

Advantageously the second dialyzer comprises a filter membrane having a cut-off value ranging from 1000-15000 Da and preferably 5000-10000 Da. Moreover the second dialyzer may be a mid-flux dialyzer having a cut-off value of 15000-20000 Da. The first dialyzer may be a high-flux dialyzer having a cut-off value of 20000-40000 Da. A dialyzer having a cut-off value of 40 kDa may also be referred to as a high-cut-off dialyzer. The values mentioned above for the second dialyzer identify a lower limit for the molecular weight and the values of the first dialyzer identify an upper limit for the clearance. The thus defined molecular range will predominantly be eliminated from the blood stream. While smaller molecules, for example electrolytes, are to be eliminated from the blood stream on a lower level and molecules which are larger in size than the above-mentioned middle molecules—such as for example albumin—are not to be eliminated from the blood stream; the range of molecular size may be set to interleukins or cytokines or other molecular sizes which are to be eliminated. A larger cut-off value for the second dialyzer of 5000 Da or 15000 Da furthermore provides for the membrane resistance thereof not to increase quite rapidly and consequently has to be exchanged.

Moreover the dialysis device may be designed such that the proportion of the permeate stream to the filtration feed is greater than 0.5 and preferably 0.8 +/− 0.1; i. e. the retentate stream will be 50% of the second dialyzer and will preferably only be 20% +/− 10%. In this way a large proportion of dialysate will be retained in the cycle, thereby reducing the amount of dialysate substitute and consequently the costs mentioned above.

As set out before the dialysis device is preferably suitable for the removal of an overproportionally high level of molecules of middle molecular masses from the blood stream in the first dialyzer. The molecules can for example be found in the range of the middle molecules from 1000 to 50000 Da and preferably from 5000 to 25000 Da wherein removal of molecules is based on the removal of molecules having smaller molecular masses, i. e. especially smaller than 1000 Da.

The ratio of the cut-off value of the second dialyzer to the first dialyzer is in the range of 1:5 to 1:40. Furthermore this ratio may be in the range of 1:8 to 1:12. The relation of the cut-off values of both dialyzers is of importance since, advantageously, the higher the cut-off value of the first dialyzer the higher the cut-off value of the second dialyzer has to be set in order to avoid premature clogging of the second dialyzer.

Moreover the portion of molecules having a mass of 15,000 Da removed from the bloodstream in the first dialyzer may be increased by at least 20% compared to the portion of molecules having a mass below 1,000 Da. By this relation it is meant that an increased level of cytokines will be removed from the blood flow compared to smaller molecules since for example cytokines have a mass of 14-17 kDa.

In a further advantageous embodiment the dialysate circuit comprises a heating device for the dialysate. Ordinarily in known dialysis processes the supplied dialysate (or dialysate substitute) will be heated to about blood temperature. Generally dialysate substitute having a concentration of bicarbonate of 35 mmol/l will be used, which is slightly higher than the concentration of bicarbonate present in the human blood. However, a high concentration of bicarbonate will be disadvantageous as it may result in precipitation with the ions present (e.g. $Mg^{++}$ or $Ca^{++}$). Thus the dialysate substitute $Q_{feed}$ may preferably be introduced into the dialysate cycle. Since the bicarbonate concentration thereof is lower (preferably by 30 mmol/l or slightly higher) an average value of bicarbonate concentration from the circulating dialysate and the introduced $Q_{feed}$ will result. If the mixture will subsequently be heated the tendency to precipitate will be reduced due to lower concentration. According to FIG. 1 the heating device (not shown) may be situated in the neighborhood of the pump. Thus, $Q_{feed}$ will at first be supplied to the dialysate circuit, then will be mixed through a particular part of the duct and will finally be heated to the blood temperature required.

Figure 3:
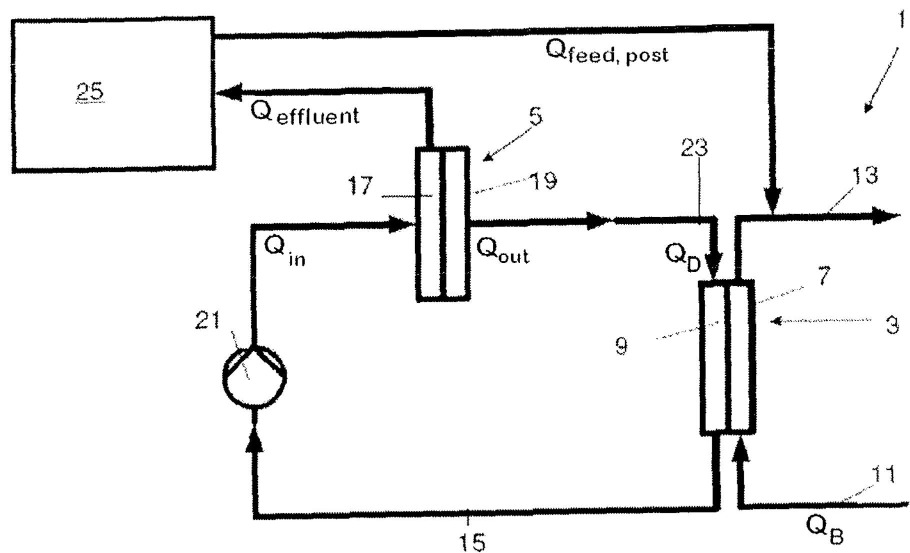
Figure 4:
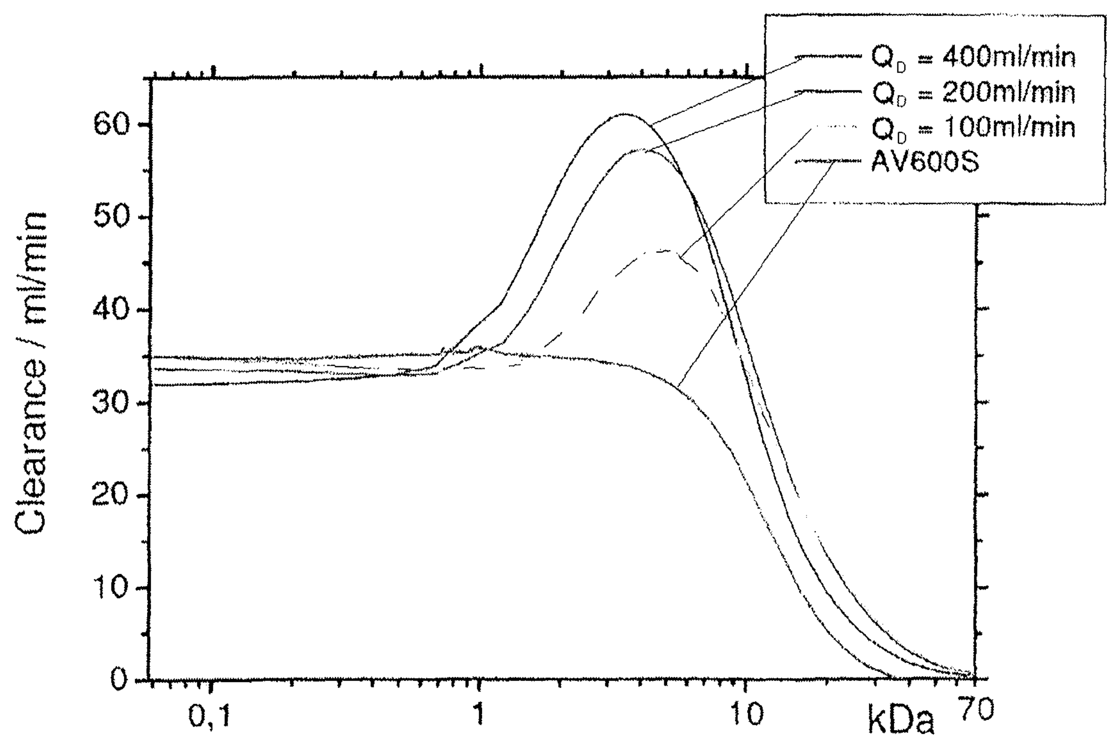

The invention will be explained in detail by way of the following figures wherein FIG. 1 to FIG. 3 each show a schematic representation of an embodiment of the dialysis device, and FIG. 4 shows a clearance diagram as exemplified by dextrans.

FIG. 1 shows a dialysis device 1 according to a first embodiment of the present invention, including a first dialyzer 3 and a second dialyzer 5. The first dialyzer 3 comprises a blood space 7 and a dialysate space 9, both spaces being separated from each other by a membrane. Dialyzers of the type described herein are generally known. They include a housing wherein several cylindrical hollow fiber membranes bundled up to a bundle of hollow fibers are provided. Blood flows through the interior of the hollow fiber membranes whereas a dialysate preferably flows in a countercurrent direction to the blood in the space between the hollow fiber membranes and the filter housing. It is understood that differently formed dialyzers may also be provided. According to the present invention, the total of those portions where a blood flow occurs in dialyzer 3 is understood by blood space 7 and the total of those portions where a dialysate flow occurs is understood by dialysate space 9.

The wall of the membrane in dialyzer 3 is formed in a semipermeable manner such that an exchange of matter may take place. In hemodialysis this will take place by way of diffusion as long as an equilibrium will be established in blood space 7 and dialysate space 9. Depending on the pore size of the membranes larger or smaller molecules will be passed to the dialysate space 9.

In operation a patient is to be connected to the dialysis device 1. The blood of the patient will enter the blood space 7 of the first dialyzer 3 via a blood feed line 11, returning to the patient via recirculation line 13.

In the dialysate space 9 of the first dialyzer 3 the dialysate preferably flows in countercurrent direction to the blood flow, as indicated by the arrows in FIG. 1. During dialysis the above-mentioned exchange of matter takes place between the blood and the dialysate, the latter subsequently exiting dialyzer 3 via conduit 15. The dialysate contains the substances which will be removed from the blood circulation $Q_B$ during dialysis.

As mentioned above removal of middle-sized molecules (herein in the following also called middle molecules) from the patient's blood circulation is of particular importance. In the present embodiment of FIG. 4 molecules having masses of 1,000 to 10,000 Da will increasingly be removed from the blood stream. In the invention molecules having masses of 1 kDa to 50 kDa or as high as 70 kDa may also be understood as middle-sized molecules.

The dialyzer will therefore be formed such that middle molecules will predominantly be removed from the blood, thus consequently the former may also diffuse into the dialysate. The dialyzer 3 is formed such that its membrane concerning pore size thereof matches the desired Dalton cut-off value wherein Dalton is a mass unit corresponding to $1.6601*10^{-27}$ kg.

Thus the membrane of the first dialyzer 3 provides for molecules exceeding the respective threshold of mass not to enter the dialysate circuit $Q_D$. As will be set forth in detail herein below the second dialyzer 5 will result in that the permeate stream $Q_{out}$ which will be recirculated to the dialysate space 9 in the form of dialysate flow $Q_{D1}$ essentially will not contain any middle sized molecules, i.e. for example having masses exceeding 6000 Da. It will rather have a certain concentration of smaller molecules. While having a low concentration gradient of small molecules (up to 1000 Da) in both compartments of the first dialyzer 3 there will only be slight permeation of molecules through the membrane within this weight range. Since, however, concentration of middle-sized molecules in the dialysate flow $Q_D$ is significantly lower than in the blood, this, as a result, will cause equalization of concentration of these of middle-mass molecules. With higher molecular masses the masses of which are above the cut-off value of the membrane of the first dialyzer 3 equalization of concentration however is inhibited due to permeability of the membrane. It will thus result in that middle-mass molecules will preferably be removed from the blood by the dialysis device.

For example dialyzer 3 may be formed as a high-flux dialyzer which is also called high-flux filter. According to the present invention a high-cut-off dialyzer which is also known in the art and which has an even higher pore size may be used as well. As a set value with high flux a cut-off value of appx. 30 kDa +/− 10 kDa may be identified and high-cut-off filters (also called enhanced middle molecule clearance filters) may have a cut-off value of 40 kDa or higher.

According to FIG. 1 the "used" dialysate passes from the first dialyzer 3 via conduit 15 into an entrance space 17 of the second dialyzer 5 as filtration feed $Q_{in}$. The permetate stream $Q_{out}$ of the second dialyzer 5, i. e. the portion of the filtration feed $Q_{in}$ permeating the membrane will be introduced into the first dialyzer 3 as $Q_D$, thus completing the dialysate circuit. Contrary to the first dialyzer which, according to the principle of hemodialysis, functions with two volume streams which preferably are in opposite direction to each other the second dialyzer 5 may also be identified as a filter separating the stream of filtration feed $Q_{in}$ into two streams, i. e. the permetate stream $Q_{out}$ and the retentate stream $Q_{effluent}$. If for example a filter having a cut-off value of 1,000 Da will be used the permetate stream $Q_{out}$, as a result, will essentially not have any molecules exceeding 1,000 Da since these will be retained on the filter and will co-exit the second dialyzer 5 with the retentate effluent $Q_{effluent}$ and will be introduced to supply means 25 where they will be retained or discarded, respectively.

Since in this way middle molecules will be removed from dialysate circuit in the second dialyzer 5 and smaller molecules, such as below the cut-off threshold thereof will be retained, the second dialyzer 5 causes partial regeneration of dialysate.

The resulting filtrate or permetate stream $Q_{out}$ consequently has a reduced number of middle molecules and will be passed to the dialysate space 9 of the first dialyzer 3 from the filtrate space 19 via conduit 23, where in turn it will be used as dialyzing fluid or dialysate, respectively. Having reduced the number of middle molecules in the second dialyzer 5 a concentration gradient between the blood in blood space 7 and the partially regenerated dialysate in dialysate space 9 will be established after recirculation of the dialysate or the filtrate, respectively, to the first dialyzer 3. The concentration gradient will result in that no equilibrium will be present between the concentration of the middle molecules in the dialysate and the blood such that in turn there will be increased diffusion of middle molecules through the membrane. This dialysate will be recirculated to the second dialyzer 5 in the dialysate circuit and finally will partially be reused as a dialysate etc. It can be seen from FIG. 1 that the dialysate circuit extends from the first dialyzer 3 via conduit 15 to the second dialyzer 5 then returning to the first dialyzer 3 via conduit 23.

The volume stream of the retentate effluent $Q_{effluent}$ which was removed from the dialysate circuit has to be supplied in the form of dialysate substitute $Q_{feed}$, the total of the retentate $Q_{effluent}$ and the amount consequently transferred in the first dialyzer thereby largely has to correspond to the dialysate substitute $Q_{feed}$ in order to maintain the amount within the dialysate circuit on a constant level. During intended volume removal from the patient's blood $Q_{effluent}$ will be set larger than $Q_{feed}$, the difference corresponding to intended volume removal.

In the second dialyzer 5 the filtration ratio $Q_{out}/Q_{in}$, i. e. the ratio of the amount of the cascade output ($Q_{out}$, i. e. the regenerated flow) to the cascade input ($Q_{in}$, i. e. the fluid fed to the cascade filter) is about 0.5 to 1, preferably 0.5 to 0.9. Accordingly the filtrate $Q_{out}$ of the second dialyzer 5 will be diluted by the dialysate substitute $Q_{feed}$ upstream (see FIG. 1) or downstream (see FIG. 2) of the first dialyzer 3 such that the percentage of low-molecular weight molecules will decrease during introduction into the dialysate space 9 of the first dialyzer 3. Consequently, introduction of dialysate substitute will also create a concentration gradient supporting diffusion of low molecular weight compounds from the blood into the dialysate in the first dialyzer 3. Clearance of the low molecular weight compounds will thus essentially be controlled by the amount of dialysate substitute.

Typical flows will be a blood flow $Q_B$ of 100-200 ml/min, a dialysate substitute $Q_{feed}$=10-100 ml/min, typically 40 ml/min and a dialysate flow $Q_D$ in the first dialyzer=100-400 ml/min, typically 200 ml/min. A filtration fraction $Q_{out}/Q_{in}$=160/200=0.8.

In the embodiment of FIG. 1 dialysate substitute $Q_{feed}$ is introduced into the dialysate circuit upstream of the second dialyzer 5 by supply means 25, seen in the flow direction of the dialysate. Introduction of the fresh solution upstream of the second dialyzer 5 is of advantage in that the second dialyzer 5 then, on the one hand, functions as a regenerator for the dialysate of the first dialyzer 3 but, on the other hand, also functions as a dialysate filter for removal of bacteria and endotoxins which are likely to be present in the dialysate substitute $Q_{feed}$. The second dialyzer 5 consequently has dual function, additionally acting as a sterile filter for the dialysate substitute $Q_{feed}$. Moreover a filter which usually is provided for purification of the fresh dialysate, i. e. the dialysate substitute, may be omitted.

The mode of operation will become more evident by way of the following example: An inflammatory mediator (having a mass of 14-17 kDa, such as cytokines) will be removed from the blood. The dialysate flow $Q_D$ has significantly lower concentration of middle molecules, i. e. in the order of the inflammatory mediator, allowing increased diffusion of these molecules into the dialysate in the first dialyzer 3. When the dialysate is introduced into the second dialyzer 5 the low cut-off value thereof, for example 1 kDa, provides for the inflammatory mediator being contained in significantly reduced concentration in the permetate stream $Q_{out}$ which exits the second dialyzer. The permetate stream $Q_{out}$ may thus be reused as a dialysate for the first dialyzer 3 in a process of circulation.

Albumin is a molecule the removal of which from the blood stream $Q_B$ is not desired. Since albumin has a Dalton molecular weight of 68 kDa it may only be removed in a clinically minor amount in the first dialyzer if the latter has a cut-off value of for example 40 kDa.

Figure 2:
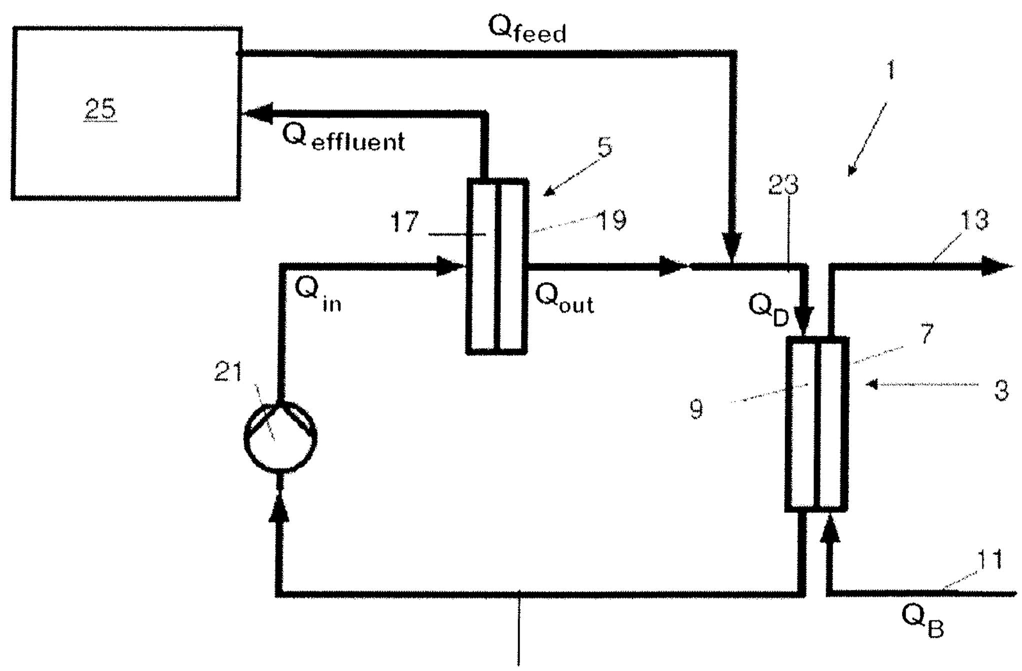

Referring to FIG. 2 a further embodiment of the present invention is shown. Equal parts are identified by equal reference numbers so that reference can be made to the description of FIG. 1 in order to avoid duplication of information.

In FIG. 2 supply means 25 are provided which are provided for the introduction of dialysate substitute to the dialysate circuit. Other than in the embodiment of FIG. 1 in FIG. 2 dialysate substitute $Q_{feed}$ is introduced via conduit 23, i. e. downstream of the second dialyzer 5, as seen in the flow direction of the dialysate. In this embodiment introduction is realized downstream of the second dialyzer 5. Consequently maximum efficiency in relation to dialysate substitute will be reached, however the dual function of the second dialyzer 5 as an additional sterile filter will be suppressed.

Furthermore, as can be seen in FIG. 3, direct introduction of fresh substitute solution preferably in postdilution into the blood of the patient rather than introduction of dialysate substitute $Q_{feed.post}$ is realized. This will take place downstream of the first dialyzer 3 as seen in the flow direction. However, the advantage of exclusively using solutions which do not come within the provisions of the Pharmaceutical Drug Law and which in consequence will be less versatile in the view of changing composition thereof will be suppressed. Alternatively (not shown) the dialysate substitute may also be introduced into the blood upstream of the first dialyzer 3 in predilution in the form of a fresh substitution solution.

The device may furthermore be operated both with systemic anticoagulation and regional anticoagulation (citrate anticoagulation).

Briefly, it can be seen that according to the present invention a cascade dialysis device and a cascade dialysis process, respectively, may be realized wherein higher clearance of middle molecules may be accomplished even at comparably low blood flow. Whereas with traditional processes, especially in postdilution, fraction of filtration is limited to 20-30% since otherwise concentration of the blood components in the dialyzer will result which may cause clotting or another damage of the blood. Moreover, in traditional processes, in the case of predilution, efficiency of the employed solution will decline due to the dilution effect as dosage will be increased.

Studies have revealed that significant increase of removal of middle molecules may be accomplished by way of cascade analysis, compared to hemofiltration having the same approach.

FIG. 4 shows an example for the mode of operation of the dialysis device by way of dextrans. With dextrans clearance may easily be identified simultaneously over a wide range of molecular sizes. A blood flow $Q_B$ of 200 ml/min was used for this series of measurements and the input of fresh dialysate (according to FIG. 1 upstream of the second dialyzer) was set to 35 ml/min. The dialysate stream $Q_D$ will be varied and will be 100 ml/min, 200 ml/min or 400 ml/min. The cut-off value of the second dialyzer 5 is 1 kDa and that of the first dialyzer is 20 kDa. In the range of 2 to 10 kDa clearance is significantly increased, i. e. the stream of molecules of middle-size order removed from the blood.

The data will be compared to hemofiltration with AV600S which according to FIG. 4 has no increased clearance value in the middle-sized order mentioned above. The example shows the basic mode of operation of the cascade dialyzer.

Features of different embodiments may optionally be combined.

LIST OF REFERENCE NUMERALS

1 dialysis device
3 first dialyzer
5 second dialyzer
7 blood space
9 dialysate space
11 blood feed
13 recirculation
15 conduit
17 entrance space
19 filtrate space
21 pump
23 conduit
25 supply device
$Q_B$ blood flow
$Q_D$ dialysate flow
$Q_{feed}$ dialysate substitute
$Q_{effluent}$ retentate effluent
$Q_{out}$ permetate stream
$Q_{in}$ filtration feed

The invention claimed is:

1. A dialysis device (1) having a. dialysate circuit comprising a first dialyzer (3) having a dialysate space (9) separate from a blood space (7) and connected in the dialysate circuit through the dialysate space (9) with a second dialyzer (5), the first dialyzer (3) being connectable to the blood circulation of a patient via a dialysis circuit comprising a blood feed line (11) to the blood space (7) and a recirculation line (13) from the blood space (7), wherein the second dialyzer (5) separates a retentate flow ($Q_{effluent}$) from a permetate stream ($Q_{out}$) and passes the permetate stream ($Q_{out}$) to the dialysate space (9) of the first dialyzer (3), the second dialyzer (5) containing a filter membrane having a cut-off value of at least 500 Da, and the first dialyzer (3) containing a filter membrane separating the dialysate space (9) from the blood space (7) and having a cut-off value higher than that of the second dialyzer (5).

2. The dialysis device according to claim l configured for introduction of a dialysate substitute ($Q_{feed}$) into the dialysate circuit in the flow direction downstream of the first dialyzer (3) and upstream of the second dialyzer (5).

3. The dialysis device according to claim 1 configured for introduction of a dialysate substitute ($Q_{feed}$) into the dialysate circuit in the flow direction downstream of the second dialyzer (5) and upstream of the first dialyzer (3).

4. The dialysis device according to claim 1 configured for introduction of a dialysate substitute into the recirculation line (13).

5. The dialysis device according to claim 1 wherein the second dialyzer (5) filter membrane has a cut-off value ranging from 1000 to 15000 Da.

6. The dialysis device according to claim 1 wherein the second dialyzer (5) is a mid-flux dialyzer having a cut-off value of the membrane of 15000-20000 Da.

7. The dialysis device according to claim 1 wherein the first dialyzer (3) is a high-flux diayzer having a cutoff value of 20000-50000 Da.

8. The dialysis device according to claim 1 configured for providing a filtration feed ($Q_{in}$) to the dialysate circuit, wherein the proportion of the permetate permeate stream ($Q,_{out}$) to the filtration feed ($Q_{in}$) is greater than 0.5.

9. The dialysis device according to claim 1 wherein the cut-off ratio of the second dialyzer (5) to the first dialyzer (3) is in the range of 1:1.5 to 1:40.

10. The dialysis device according to claim 9 wherein the cut-off ratio of the second dialyzer (5) to the first dialyzer (3) is in the range of 1:2 to 1:10.

11. The dialysis device according to claim 1 wherein clearance from the blood stream effected in the first dialyzer (3) of molecules of molecular masses of 15000 Da is at least 20% higher than clearance from the blood stream effected in the first dialyzer of molecules of molecular masses below 1000 Da.

12. The dialysis device according to claim 1 further having means for introducing a dialysate substitute into the dialysate circuit, wherein the dialysate circuit further comprises a heating device for the dialysate substitute.

* * * * *